(12) United States Patent
Iverson et al.

(10) Patent No.: US 11,766,509 B2
(45) Date of Patent: Sep. 26, 2023

(54) HEAT CONDUCTIVE CIRCUIT

(71) Applicant: MOZARC MEDICAL US LLC, Minneapolis, MN (US)

(72) Inventors: Michelle A. Iverson, Roseville, MN (US); Alexa R. Brigman, Coon Rapids, MN (US)

(73) Assignee: Mozarc Medical US LLC, Minneapolis, MN (US)

( * ) Notice: Subject to any disclaimer, the term of this patent is extended or adjusted under 35 U.S.C. 154(b) by 102 days.

(21) Appl. No.: 17/223,687

(22) Filed: Apr. 6, 2021

(65) Prior Publication Data

US 2022/0313880 A1 Oct. 6, 2022

(51) Int. Cl.
| | |
|---|---|
| *A61M 1/16* | (2006.01) |
| *H05K 7/20* | (2006.01) |
| *A61J 1/14* | (2023.01) |
| *A61J 1/10* | (2006.01) |
| *A61M 1/28* | (2006.01) |

(52) U.S. Cl.
CPC ............ *A61M 1/1664* (2014.02); *A61J 1/10* (2013.01); *A61J 1/14* (2013.01); *A61M 1/1629* (2014.02); *H05K 7/20281* (2013.01); *A61M 1/28* (2013.01); *A61M 2205/3368* (2013.01); *A61M 2205/366* (2013.01); *A61M 2210/1017* (2013.01)

(58) Field of Classification Search
None
See application file for complete search history.

(56) References Cited

U.S. PATENT DOCUMENTS

2012/0063973 A1\* 3/2012 Ang .................. A61M 5/44
422/555

\* cited by examiner

*Primary Examiner* — Krishnan S Menon
(74) *Attorney, Agent, or Firm* — Shumaker & Sieffert, P.A.

(57) ABSTRACT

A container system configured to transfer heat to a fluid contained within the container system, such as dialysate. The container system may be configured to fluidly couple to a medical machine. The container system includes a flexible material comprising a wall of the container system. In examples, the flexible material defines a container volume configured to contain the fluid. The flexible material mechanically supports a circuit configured to generate and transfer heat to the fluid. The circuit is configured to flex and/or bend when the flexible material flexes and/or bends. In examples, the container system includes control circuitry configured to cause the circuit to generate heat based on a temperature of the fluid.

17 Claims, 5 Drawing Sheets

HEAT CONDUCTIVE CIRCUIT

TECHNICAL FIELD

This disclosure is related to a heat conductive circuit configured to heat a fluid, such as a medical solution in a flexible medical solution bag.

BACKGROUND

Dialysis machines may be used to remove waste products from blood of a patient when the kidneys of the patient are no longer able to adequately do so. During dialysis, the dialysis machine may generate or regenerate dialysate using specified concentrations of solute buffers, osmotic agents, cations, and other concentrates for biocompatibility with the patient. The dialysis machine may provide the dialysate to a cycler for delivery to the patient. For example, the cycler may deliver the dialysate through a catheter into a peritoneal cavity of the patient. Toxins and metabolic waste products are exchanged from the blood of the patient to the dialysate. The dialysate including the toxins and waste products may be removed and discarded.

SUMMARY

This disclosure describes a container system configured to transfer heat to a fluid contained within the container system, such as a fluid comprising dialysate. The container system may be configured to fluidly couple to a medical machine (e.g., a peritoneal dialysis machine) configured to supply the dialysate to the peritoneal cavity of a patient. The container system includes a circuit configured to generate and transfer heat to the fluid. The circuit is mechanically supported by a flexible material of a wall of the container system, such as a flexible wall of a medical solution bag. The container system is configured such that, when the wall flexes as a result of movement of some portion of the container system, flow of a fluid through the container system, inadvertent contact with the container system by another object or a person, or some other reason, the circuit also flexes with wall in a manner preserving the ability of the circuit to generate and deliver heat to the fluid. The container system may be configured to transfer heat to the fluid to aid in generating a medical solution for use by the patient, and/or to heat the solution to increase the comfort of the patient.

In an example, a container system for delivering a medical solution comprising a fluid for use in a patient comprises: a wall configured to transfer heat to a container volume configured to hold the fluid, wherein the wall comprises a flexible material; and a circuit mechanically supported by the flexible material, wherein the circuit is configured to flex with the flexible material, and wherein the circuit is configured to receive electrical power and generate heat using the electrical power to heat the fluid held within the container volume.

In an example, a container system for heating and delivering a medical solution comprising a fluid for use in a patient comprises: a wall configured to transfer heat to a container volume configured to hold the fluid, wherein the wall comprises a flexible material; a circuit mechanically supported by the flexible material, wherein the circuit is configured to flex with the flexible material, and wherein the circuit is configured to receive electrical power and generate heat using the electrical power to heat the fluid held within the container volume; a temperature sensor configured to sense a temperature of the fluid held in the container volume; and control circuitry configured to cause the circuit to generate the heat, wherein the control circuitry is configured to: receive a temperature signal indicative of a temperature of the fluid sensed from the temperature sensor, and cause the circuit to generate the heat based on the temperature signal.

In an example, a method comprises: generating heat using a circuit receiving electrical power and mechanically supported by a wall comprising a flexible material and defining a container volume holding a fluid; and heating the fluid in the container volume using the heat from the circuit.

The details of one or more examples are set forth in the accompanying drawings and the description below. Other features, objects, and advantages will be apparent from the description and drawings, and from the claims.

DETAILED DESCRIPTION

This disclosure describes a container system configured to deliver a medical solution comprising a fluid to provide therapy to a patient. The container system includes a circuit configured to generate and transfer heat to the fluid prior to delivery of the medical solution to the patient. For example, the container system may be configured to deliver dialysate to a medical system configured to provide the dialysate to the peritoneal cavity of a patient. The circuit may be configured to transfer heat to the dialysate prior to the dialysate entering the patient, such that the dialysate has a temperature similar to the body temperature of the patient.

In examples, the container system defines a container configured to hold a solid solute (e.g., a powdered dialysis concentrate). The container system may be configured to receive a fluid solvent (e.g., purified water) in the reservoir and mix the solvent and the solute to generate a solution (e.g., a dialysis solution). The circuit may be configured to transfer heat to the solvent and/or the solvent/solute mixture to aid in generating the solution, and/or to heat the solution to increase the comfort of a patient. For example, the container system may be configured for use with a home peritoneal dialysis machine intended to be operated by a patient or another user (e.g., a care giver). The container system may be configured to ship to the patient along with a powdered dialysis concentrate within the container system. The container system may be configured such that a medical machine (e.g., a home Peritoneal Dialysis ("PD") machine) enables the addition of purified water or another solvent to the reservoir of the container system, such that the container system causes mixing of the solvent and dialysis concentrate to produce a dialysis solution. The circuit may be configured to heat the solvent and/or the dialysis solution to aid in generating the solution and/or increase the comfort of the patient as the dialysis solution is administered.

The circuit is mechanically supported by a flexible material of a wall of the container system. The wall of the container system is configured to transfer heat to a container volume. The container volume is configured to contain the fluid. The container volume may be a reservoir or some other portion of the container system configured to contain the fluid. The wall mechanically supporting the circuit may define the container volume. In examples, the container volume is a lumen of an inlet conduit (e.g., entry tubing) configured to provide a solvent to the reservoir of the container system. The circuit may be configured to transfer heat to the solvent as the solvent flows through the lumen prior to mixing with the solute. The container volume may be the fluid reservoir (e.g., a volume defined by a bag fluidly coupled to the entry tubing) configured to contain the solution prior to providing an outflow of the solution to deliver patient therapy. The circuit may be configured to transfer heat to the solution as the fluid reservoir contains the solution prior to outflow. The container volume may be defined by a lumen of an outlet conduit (e.g., outlet tubing fluidly coupled to a bag of the container system) configured to provide the outflow of the solution. The circuit may be configured to transfer heat to the solution as the solution flows through the outlet lumen. In some examples, the wall mechanically supporting the circuit defines a covering configured to cover a portion of the container volume to transfer heat to the fluid held within the container volume. The circuit may be configured to transfer heat to any fluid within the container system, including fluids comprising mixtures, fluid comprising suspensions, and/or fluids with an substantial absence of a solute.

The wall including the flexible material mechanically supporting the circuit may be configured to bend and/or flex. The flexible material of the wall may be configured to flex when the wall flexes. For example, the wall may be a wall of flexible entry tubing fluidly coupled to a fluid reservoir defined by the container, a wall of a flexible bag defining the fluid reservoir, or a wall of flexible outlet tubing fluidly coupled to the fluid reservoir. The circuit is configured to flex when the flexible material flexes (e.g., to flex with the flexible material). In examples, the circuit includes one or more circuit elements configured to generate the heat when the circuit receives electrical power. The circuit may be configured to flex in a manner maintaining electrical connectivity between the one or more circuit elements when the substrate flexes with the flexible material wall. Hence, the container may be configured such that the circuit retains an ability to generate heat using the one or more circuit elements as the circuit flexes with the wall during, for example, shipping of the container, use by a patient or a care-giver, or other use of the container.

As used herein, when a material flexes (e.g., the flexible material comprising the wall and/or a circuit substrate), this may mean a deflection and/or a bending of a surface defined by the material. The material may deflect and/or bend in response to a force applied to the material. For example, the flexible material comprising the container system may exhibit an ability to flex and/or bend when a force is applied to the flexible material as a result of movement of some portion of the container system, flow of a fluid through the container system, inadvertent contact with the container system by another object or a person, or some other reason. In examples, the flexible material defines the container volume of the container system, and deflection and/or bending of the flexible material causes the container volume to alter its defined shape, internal proportions, and/or volumetric capacity. In examples, the flexible material comprising the container system mechanically supports the circuit, and the circuit is configured to deflect and/or bend when the flexible material deflects and/or bends.

The circuit is configured to receive electrical power and generate heat using the electrical power. The circuit may be configured to generate heat when the one or more circuit elements receive the electrical power. In examples, the circuit includes a heating element configured to generate the heat. For example, the heating element may include one or more resistive heating elements configured to generate heat in response to a current driven by the electrical power. The circuit may be configured such that the heating element transfers the heat to the fluid through the wall of the container defining the container volume. For example, the container system may include a container body (e.g., a bag) defining a reservoir configured to contain the fluid (e.g., the fluid in a medical solution), an inlet conduit (e.g., inlet tubing) configured to provide a flow path for the fluid into the reservoir, and an outlet conduit (e.g., outlet tubing) configured to provide a flow path for the fluid out of the reservoir and to a medical machine and/or a patient. The circuit may be configured such that the heating element generates and transfers heat through a wall of the inlet conduit, a wall of the container body, and/or a wall of the outlet conduit.

The container system may include control circuitry configured to cause the circuit to generate the heat. The control circuitry may be configured to receive a temperature signal indicative of a temperature of the fluid from a temperature sensor. The control circuitry may be configured to cause the circuit to generate heat based on the temperature signal. In examples, the container includes a temperature sensor configured to sense a temperature indicative of the temperature of the fluid and communicate the temperature signal to the control circuitry. The temperature sensor may be configured to sense the indicative temperature of a fluid at some location within the container system, although this is not required. For example, when the container system includes the inlet conduit, the container body, and the outlet conduit, the temperature sensor may be configured to sense an indicative temperature of a fluid within one or more of the inlet conduit, the reservoir defined by the container body, or the outlet conduit. In other examples, the temperature sensor may be configured to sense an indicative temperature of the fluid upstream of the container system (e.g., prior to the fluid entering the inlet conduit) or downstream of the container system (e.g., subsequent to the fluid exiting the outlet conduit).

In examples, the control circuitry is configured to receive the temperature signal from the temperature sensor and compare the temperature signal to a temperature setpoint. The temperature setpoint may describe a specific temperature of the fluid. The control circuitry may be configured to cause the circuit (e.g., the heating element) to generate heat based on the comparison of the temperature signal and the temperature setpoint. In examples, the control circuitry is configured to receive a setpoint signal from a thermostat)

and establish the temperature setpoint based on the setpoint signal. In some examples, the container system includes the thermostat.

Hence, the container system may be configured to transfer heat to a fluid held within a volume defined by the container system using a circuit mechanically supported by a flexible material within a wall of the container system. The circuit may be configured to transfer the heat through the wall of the container system to the fluid. The circuit is configured to flex when the flexible material flexes. In examples, the container system is configured to hold a solid solute such as a powdered dialysis concentrate and receive a fluid solvent such as purified water. The container system may be configured to transfer heat to the solvent to aid in generating a medical solution using the solute, and/or to transfer heat to the medical solution to increase the comfort of a patient. In some examples, the container system is configured to maintain a temperature of the fluid according to a temperature setpoint. For example, the container system may be configured to maintain the temperature of the fluid at a temperature of about 37 degrees Celsius (98.6 degrees Fahrenheit) or another temperature substantially matching an internal body temperature of a patient.

Figure 1:
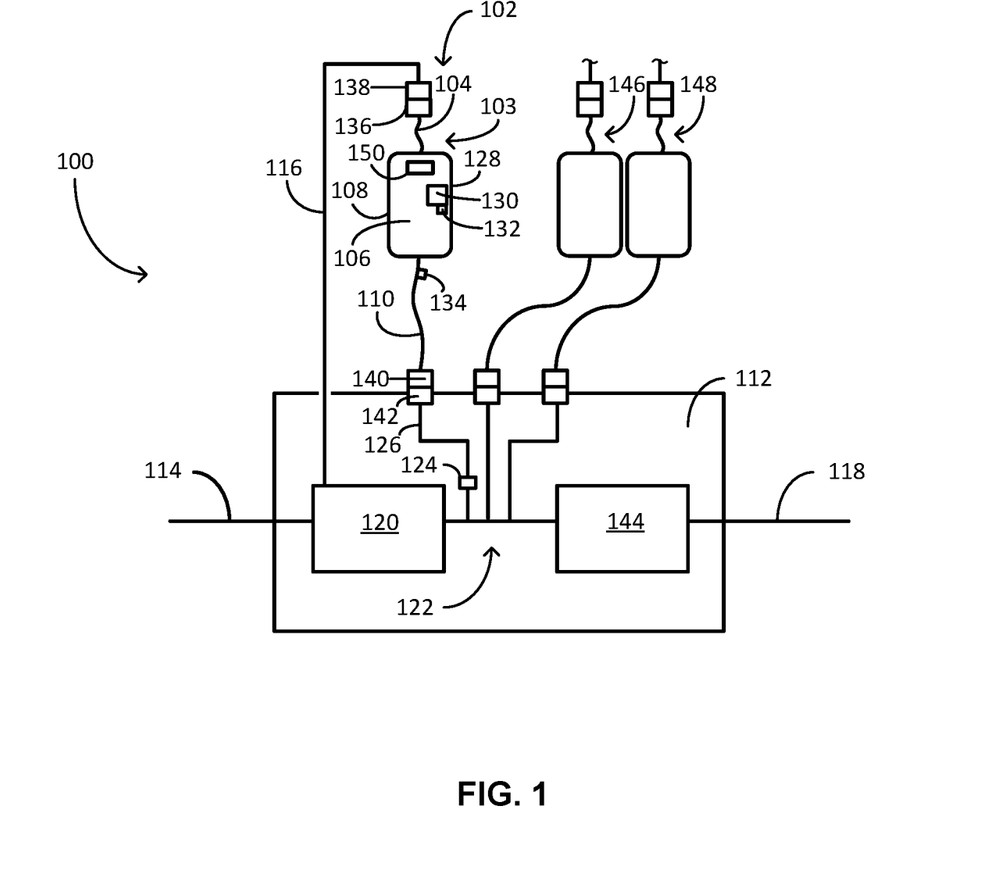
FIG. 1 is a conceptual diagram illustrating an example medical system configured to deliver a medical fluid such as dialysate.

FIG. 1 is a block diagram illustrating an example medical system 100 using a container system 102. Container system 102 includes a container 103 defining an inlet conduit 104 fluidly coupled to a reservoir 106, a container body 108 defining reservoir 106, and an outlet conduit 110 fluidly coupled to reservoir 106. Container system 102 is configured such that a fluid may inflow into reservoir 106 through an inflow lumen defined by inlet conduit 104. Container system 102 is configured such that the fluid may outflow from container 103 to a medical machine 112. In examples, container system 102 is configured to hold a concentrate (e.g., a solute in solid or liquid form) in reservoir 106. In examples, the solute includes an osmotic agent such as glucose, dextrin, and/or icodextrin. In examples, the solute includes an ion such as sodium chloride, sodium lactate, magnesium chloride, calcium chloride, potassium chloride, and/or sodium bicarbonate. Container system 102 may be configured to receive a solvent (e.g., purified water) in reservoir 106 via inlet conduit 104 and deliver a medical solution of the solute and the solvent to medical machine 112 via outlet conduit 110. In examples, container system 102 is configured to both receive a fluid inflow and provide a fluid outflow from a single conduit (e.g., outlet conduit 110 and/or inlet conduit 104).

Medical machine 112 is configured to provide therapy (e.g., dialysis) to a patient using the medical solution from container system 102. In examples, medical machine 112 may be configured to cause container system 102 to generate the medical solution. For example, medical machine 112 may be configured to receive a fluid via machine inlet conduit 114 and provide the fluid to inlet conduit 104 of container system 102 using machine fluid line 116. Container system 102 may generate the medical solution using the fluid delivered via machine fluid line 116 and deliver the medical solution produced to medical machine 112 via outlet conduit 110. In some examples, container system 102 may be configured to utilize a single fluid path for both an injection of fluid (e.g., purified water) into container system and extraction of a medical solution. For example, container system 102 may be configured to receive the fluid via a machine solution line 126 and outlet conduit 110 in a first flow direction to generate a medical solution, and then supply the medical solution via outlet conduit 110 and machine solution line 126 in a second flow direction opposite the first flow direction. Medical machine 112 may use the medical solution produced to deliver a medicinal fluid (e.g., dialysate) via an infusion line 118. In examples, infusion line 118 is configured to provide dialysate to a cycler configured to provide therapy to a patient using the dialysate, or to a container configured to retain the dialysate for subsequent use.

Medical system 100 may include a conditioning system 120 configured to provide a portion of the fluid received via machine inlet conduit 114 to inlet conduit 104 of container system 102 (e.g., via machine fluid line 116). Conditioning system 120 may be configured to provide another portion of the fluid received to a generation flow path 122 defined by medical machine 112. Conditioning system 120 may include, for example, one or more pumps configured to provide a motive force to the fluid received via infusion line 118 to drive the fluid through machine fluid line 116 and/or generation flow path 122. In some examples, conditioning system 120 may include one or more filters and/or sorbent cartridges configured to remove impurities (e.g., particulate matter and/or ions) from the fluid prior to the fluid entering container system 102, machine fluid line 116, and/or generation flow path 122. In addition, in some examples, conditioning system 120 may include one or more sensors, such as a conductivity sensor and/or a pressure sensor, configured to monitor a physical state or condition of the fluid prior to the fluid entering container system 102, machine fluid line 116, and/or generation flow path 122. In examples, conditioning system 120 includes a degasser configured to degas the fluid prior to entering container system 102, machine fluid line 116, and/or generation flow path 122. The degasser may include, for example, a vacuum pump configured to create a vacuum to remove air and other gases from the fluid received via machine inlet conduit 114.

Medical system 100 is configured to generate the medicinal fluid issued via infusion line 118 using the medical solution provided by container system 102. In examples, medical system 100 includes one or more concentrate pumps such as concentrate pump 124 configured to inject the medical solution from container system 102 into generation flow path 122 via a machine solution line 126. In some examples, medical system 100 may include one or more additional filters (not shown) configured to filter the medical solution provided from container system 102 prior to the medical solution entering generation flow path 122.

Container system 102 includes a wall 128 configured to transfer heat to a fluid within a container volume of container 103. The container volume is configured to contain the fluid. In examples, wall 128 defines a portion of container 103, such as a portion of inlet conduit 104, container body 108, and/or outlet conduit 110. In examples, wall 128 defines the container volume. For example, FIG. 1 illustrates wall 128 defining reservoir 106 as the container volume, although wall 128 may define the container volume in other portions of container system 102 in other examples. For example, wall 128 may define a container volume within the lumen of inlet conduit 104, within the lumen of outlet conduit 110, or other locations within container system 102. Wall 128 comprises a flexible material configured to flex and/or bend when a force is exerted on wall 128 (e.g., a force resulting from movement of some portion of container system 102, flow of a fluid through container system 102, inadvertent contact with container system 102 by another object or a person, or some other reason). In examples, wall 128 is wall of a flexible bag comprising container body 108 and defining reservoir 106. In some examples, wall 128 is a wall of a flexible tubing comprising inlet conduit 104 or outlet conduit 110.

The flexible material of wall 128 mechanically supports a circuit 130 configured to receive electrical power and generate heat. Circuit 130 is configured to transfer the heat to the fluid within some portion of container system 102. For example, circuit 130 may be configured to transfer the heat to fluid within a lumen defined by inlet conduit 104, reservoir 108 defined by container body 108, and/or a lumen defined by outlet conduit 110. Circuit 130 is configured to flex with the flexible material and/or wall 128. In examples, circuit 130 includes a conductor and one or more circuit elements (e.g., resistive heating elements) in electrical communication with the conductor, and circuit 130 is configured such that the one or more circuit elements maintain the electrical communication when circuit 130 flexes with the flexible material and/or wall 128.

Container system 102 may include control circuitry 132 configured to cause circuit 130 to generate the heat. In examples, control circuitry 132 is configured to provide the electrical power to circuit 130. Control circuitry 132 may be configured to cause circuit 130 to generate the heat in response to a temperature signal from a temperature sensor 134 signal indicative of a temperature of the fluid from a temperature sensor, such as temperature sensor 134. Temperature sensor 134 may be configured to sense the temperature indicative of a temperature of the fluid. Temperature sensor 134 may be configured to sense an indicative temperature of the fluid at any location. For example, temperature sensor 134 may be configured to sense a temperature indicative of the temperature of a fluid within outlet conduit 110, reservoir 106, inlet conduit 104, machine solution line 126, machine fluid line 116, infusion line 118, some other location within medical machine 112, or any other location. Control circuitry 132 may be configured to receive the temperature signal and cause circuit 130 to generate heat based on the temperature signal. In examples, control circuitry 132 is configured to receive a temperature setpoint (e.g., from a thermostat) and compare the temperature setpoint and the temperature indicated by the temperature signal. Control circuitry 132 may be configured to cause circuit 130 to generate heat for heat the fluid based on the comparison.

Container system 102 may be a substantially disposable system configured to attach and/or detach from medical machine 112. For example, container system 102 may include a first fluid connector 136 configured to mate with a connector 138 of medical machine 112 to fluidly couple container system 102 (e.g., inlet conduit 104) and medical machine 112. Container system 102 may include a second fluid connector 140 configured to mate with a connector 142 of medical machine 112 to fluidly couple container system 102 (e.g., outlet conduit 110) and medical machine 112. First fluid connector 136 and/or second fluid connector 140 may be configured such that a patient or care-giver may connect container system 102 to medical machine 112 in preparation for use of the medical solution provided by container system 102. First fluid connector 136 and/or second fluid connector 140 may be configured such that a patient or care-giver may disconnect container system 102 from medical machine 112 to dispose of or otherwise separate container system 102 from medical machine 112. In examples, first fluid connector 136 and/or second fluid connector 140 are configured to mate with medical machine 112 in response to a force applied by hand or a hand tool.

In examples, container system 102 is configured to hold a solute and generate a solution when container system receive a solvent. The solute may be, for example, a powdered dialysis concentrate, or some other solid and/or liquid solute configured to form a solution and/or mixture with the solvent. Container system 102 may be configured to receive the solvent via inlet conduit 104 and/or outlet conduit 110 and mix the solvent and the solute to generate the solution within reservoir 106. In examples, container system 102 includes a solute container 150 configured to hold the solute. Container system 102 may be configured to ship to the patient along with the solute within container 150. Container system 102 may be configured such that medical machine 112 enables addition of the solvent to reservoir 106 (e.g., via machine fluid line 116 and inlet conduit 104 and/or machine solution line 126 and outlet conduit 110), such that container system 102 causes mixing of the solvent and the solute to produce the solution. Container system 102 may be configured to deliver the solution to medical machine 112 (e.g., via outlet conduit 110 and machine solution line 126). Circuit 130 may be configured to heat the solvent and/or the solution to aid in generating the solution within reservoir 106 and/or to increase the comfort of the patient as the solution is administered.

Medical system 100 may further include a mixing system 144 configured to provide the medicinal fluid prepared using the medical solution from container system 102 to infusion line 118. In examples, mixing system 144 includes a mixing chamber configured to further mix the concentrate from container system 102 and the fluid from conditioning system 120. Mixing system 144 may include one or more sensors configured to evaluate one or more physical characteristics of the medical solution, such as one or more of conductivity sensors, pH sensors, pressure sensors, flow sensors, or the like. In some examples, mixing system 144 includes one or more sterilization units, such as one or more ultrafilters, microbial filters, UV light sources, or other sterilization units configured to substantially sterilize dialysate prior to infusion into a patient. Further, medical system 100 may be configured to receive medical solutions from other container systems, such as container system 146 and container system 148. Container systems 146, 148 may be configured similarly to container system 102, although this is not required.

Hence, container system 102 may be configured to deliver a medical solution comprising a medical machine 112 or a patient to provide therapy to the patient. In examples, container system 102 is configured to deliver a dialysate solution for use in the peritoneal cavity of the patient. Container system 102 may generate and transfer heat to a fluid comprising the medical solution to aid in generating the medical solution and/or increase the comfort of the patient as the peritoneal dialysis is administered.

Figure 2:
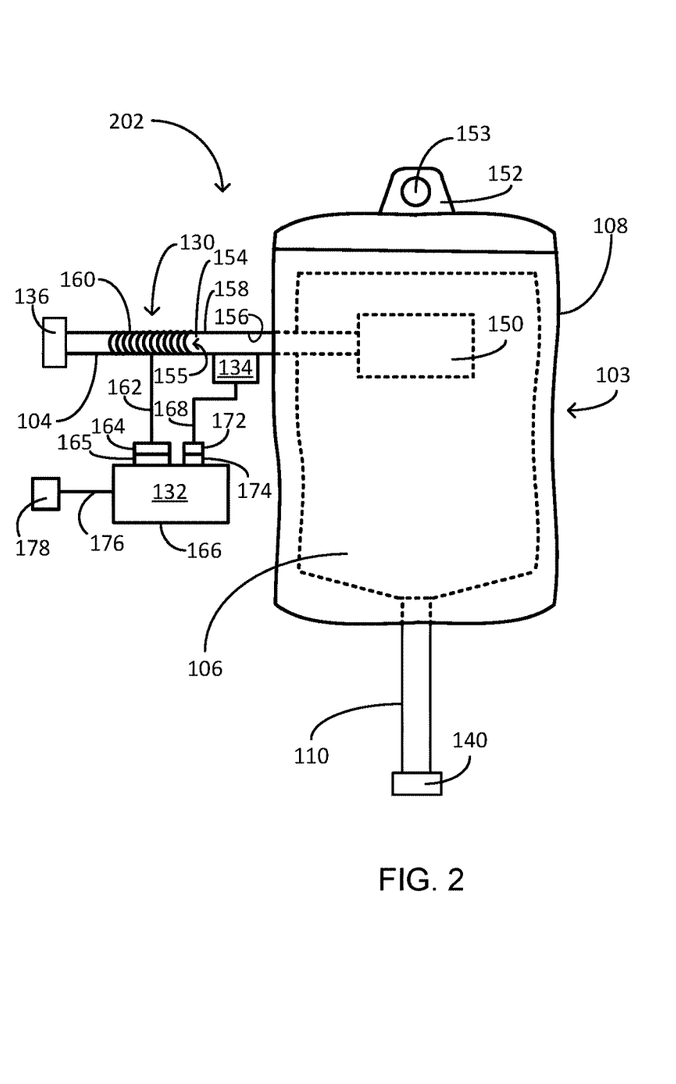
FIG. 2 is a conceptual diagram of an example container system including a circuit configured for an inlet conduit of a container.
Figure 3:
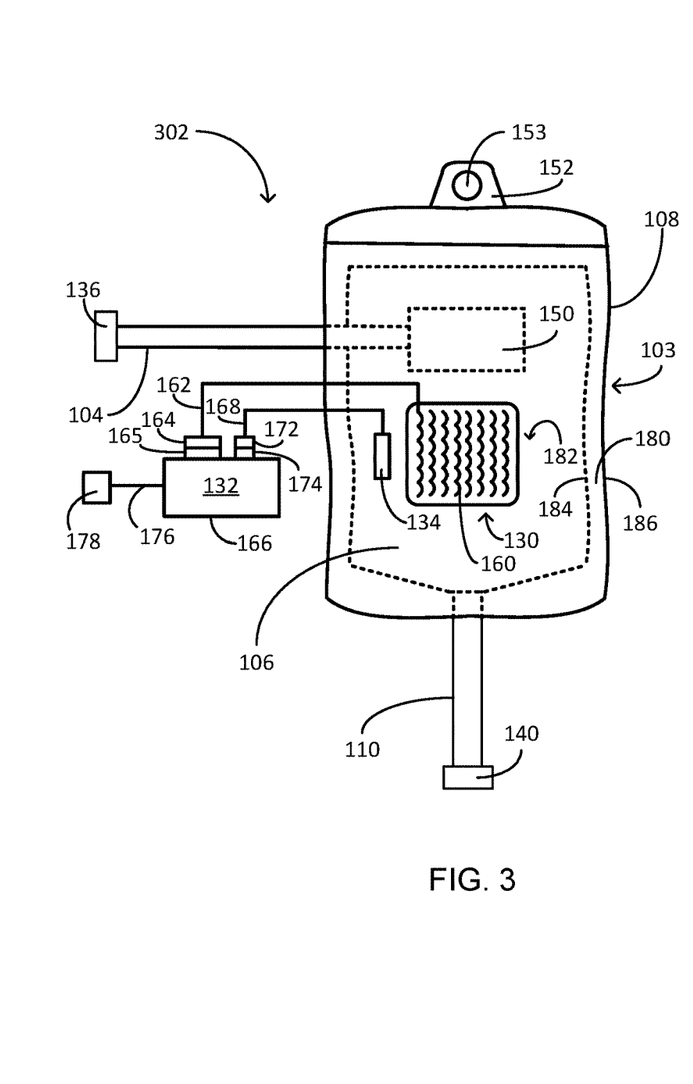
FIG. 3 is a conceptual diagram of an example container system including a circuit configured for a container body.
Figure 4:
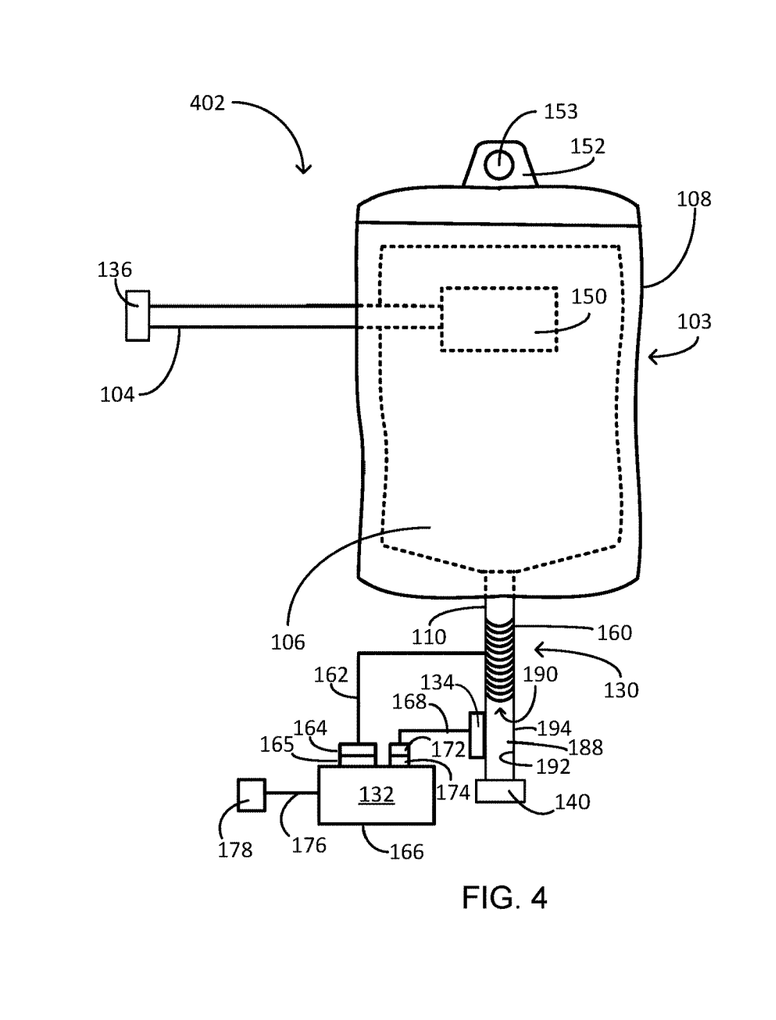
FIG. 4 is a conceptual diagram of an example container system including a circuit configured for an outlet conduit of a container.
Figure 5:
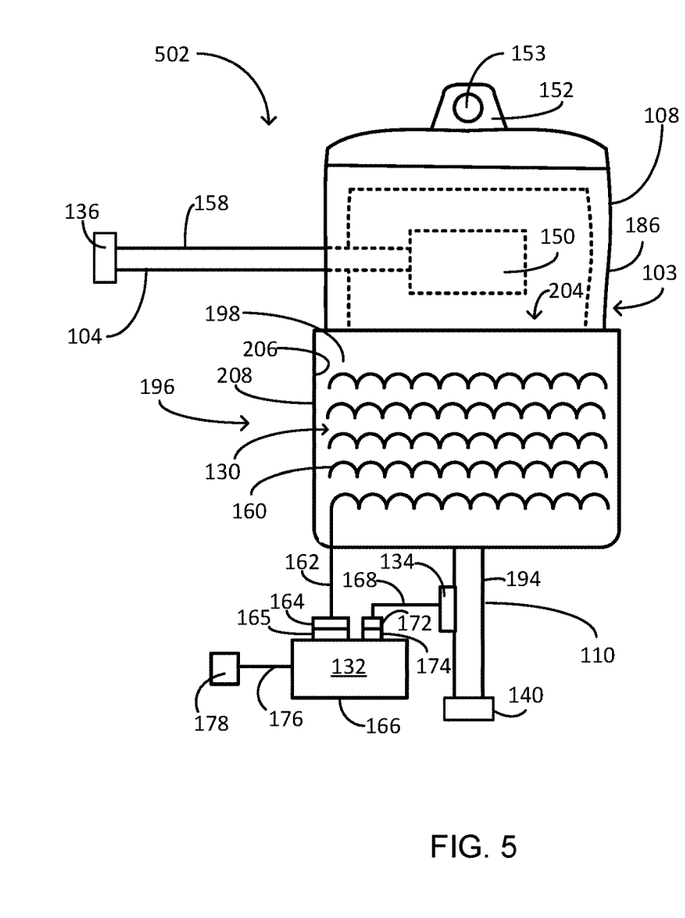
FIG. 5 is a conceptual diagram of an example container system including a circuit configured for basket defining a pouch.
Figure 6:
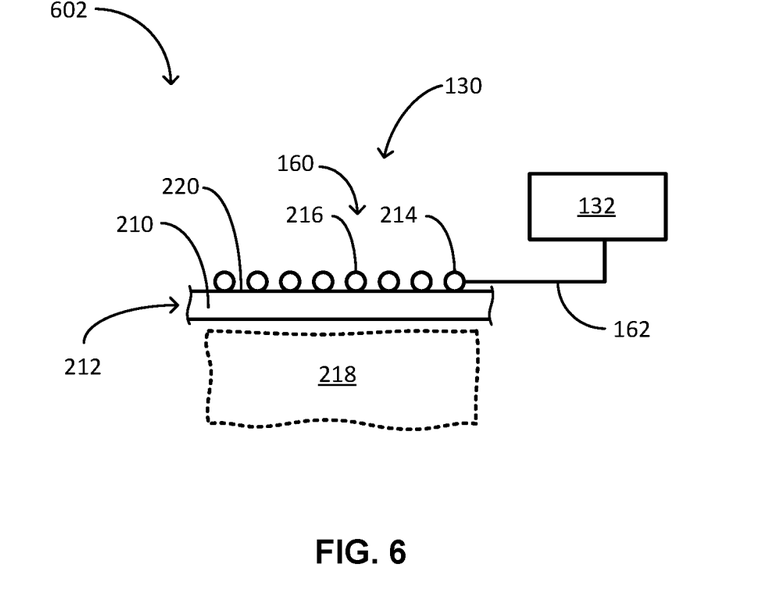
FIG. 6 is a conceptual diagram of an example container system including a circuit and circuit elements.
Figure 7:
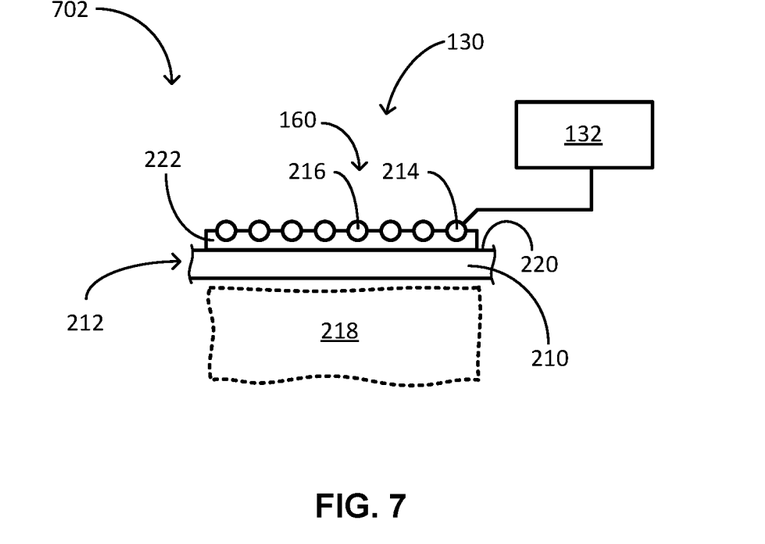
FIG. 7 is a conceptual diagram of an example container system including a circuit and a circuit substrate.

FIG. 2 illustrates an example container system 202 configured to transfer heat to a fluid within inlet conduit 104 of container 103. FIG. 3 illustrates an example container system 302 configured to transfer heat to a fluid within reservoir 106 of container body 108. FIG. 4 illustrates an example container system 402 configured to transfer heat to a fluid within outlet conduit 110 of container 103. FIG. 5 illustrates an example container system 502 defining a covering configured to transfer heat to a fluid within container 103. FIG. 6 illustrates a container system 602 including circuit 130, and FIG. 7 illustrates a container system 702 including a circuit substrate 222. Container system 202, container system 302, container system 402, container system 502, container system 602, and container system 702 are examples of container system 102. Further, the various numbered elements of container system 102, container system 202, container system 302, container system 402, container system 502, container system 602, and container system 702 may be configured individually and in relation to each other in the same manner as that described for any of container system 102, container system 202, container system 302, container system 402, container system 502, container system 602, or container system 702.

Container system 202, 302, 402, 502 is configured to deliver a fluid (e.g., a medical solution) from container body 108 to a medical machine (e.g., medical machine 112 (FIG. 1)) or a patient to provide therapy to the patient. In examples, container body 108 is a medical solution bag configured to hold a medical solution within reservoir 106. Inlet conduit 104 and/or outlet conduit 110 may be defined by flexible tubing fluidly coupled to reservoir 106. In some examples, container 103 defines a support section 152 configured to engage (e.g., mechanically engage) a support structure (not shown) such as a stand to substantially secure some portion of container 103 relative to the support structure. In examples, support section 152 defines an opening 153 configured to receive a portion of the support structure. Opening 153 may be configured to receive a portion of a hook (e.g., the bend) defined by the support structure to substantially secure the portion of container 103 relative to the support structure. In examples, support section 152 is configured to support the weight of container system 102 and/or some amount of a fluid within container system 102. Container system 102 may be configured such that, when support section 152 substantially secures the portion of container 103 to the support structure, a gravity vector acting on a fluid within reservoir 106 tends to cause the fluid to flow from reservoir 106 and through the lumen defined by outlet conduit 110.

Referring to FIG. 2, container system 202 is configured to transfer heat to a fluid within inlet conduit 104 of container 103. Inlet conduit 104 of container system 202 includes an inlet conduit wall 154. Inlet conduit wall 154 is an example of wall 128 (FIG. 1). Inlet conduit wall 154 defines a container volume 155 within the lumen of inlet conduit 104. Container volume 155 may be fluidly coupled to reservoir 106. Inlet conduit wall 154 includes a flexible material configured to flex and/or bend. The flexible material may define inlet conduit wall 154. In examples, inlet conduit 104 is flexible tubing and inlet conduit wall 154 is a wall of the tubing. Inlet conduit wall 154 may be configured such that flexible tubing of inlet conduit 104 deflects and/or bends in response to a force applied to inlet conduit 104, or a force originating elsewhere in container 103 and transmitted to inlet conduit 104 (e.g., due to movement of some portion of container system 202 from flow of a fluid, inadvertent contact by another object or a person, or some other reason).

Inlet conduit wall 154 is configured to transfer heat to a fluid within container volume 155. In examples, inlet conduit wall 154 defines an inner surface 156 defining the lumen of inlet conduit 104 and an outer surface 158 opposite inner surface 156. Inner surface 156 may be configured to contact a fluid flowing within container volume 155 to transfer heat to the fluid (e.g., by convection). Inlet conduit wall 154 is configured such that heat may transfer from outer surface 158, through inlet conduit wall 154, and to inner surface 156 when inlet conduit wall 154 transfer heat to the fluid within container volume 155. In examples, inlet conduit wall 154 is configured to transfer heat through the flexible material comprising inlet conduit wall 154 when inlet conduit wall 154 transfers heat to the fluid within container volume 155. Outer surface 158 may be an exterior surface of inlet conduit 104.

Container system 202 includes circuit 130 configured to generate heat and transfer the heat to inlet conduit wall 154, such that inlet conduit wall 154 may transfer the heat to the fluid within container volume 155. Circuit 130 is configured to receive electrical power to generate the heat. Circuit 130 may include one or more circuit elements 160 configured to generate the heat when circuit 130 receives the electrical power. Circuit elements 160 may include, for example, heating elements configured to generate the heat when circuit 130 receives the electrical power. In examples, circuit 130 is configured to receive the electrical power via a conductor 162 electrically coupled to circuit elements 160. Conductor 162 may be configured to electrical couple to a power supply. In some examples, control circuitry 132 includes and/or receives the electrical power from the power supply and provide the power to circuit 130 and/or conductor 162. In some examples, conductor 162 is electrically coupled to an electrical connector 164, and electrical connector 164 is configured to mechanically mate with an electrical connector 165 to establish the electrical coupling between electrical connector 164 and control circuitry 132 and/or the power supply.

Circuit 130 is configured to alter an amount of the heat generated when circuit 130 receives the electrical power. For example, circuit 130 may be configured to alter a rate at which the heat generates (e.g., a wattage) when circuit 130 receives the electrical power in order to, for example, alter the heat flux delivered to the fluid within container 103 (e.g., within container volume 155). In examples, circuit elements 160 are configured to alter the heat generation rate. For example, circuit elements 160 may include a resistive heating element configured to increase the heat generation rate when a current supplied to the resistive heating element increases. The resistive heating element may be configured to decrease the heat generation rate when a current supplied to the resistive heating element decreases. In some examples, circuit 130 includes a plurality of circuit elements configured to energize and deenergize independently to alter the heat generation rate. For example, circuit 130 may be configured to energize a first circuit element to provide a first heat generation rate and energize the second circuit element to provide a second heat generation rate different from the first heat generation rate.

Circuit 130 is mechanically supported by the flexible material of inlet conduit wall 154. In examples, the flexible material mechanically supporting circuit 130 defines the outer surface 158 of inlet conduit wall 154. Circuit 130 is configured to flex and/or bend when the flexible material flexes and/or bends (e.g., in response to a force applied to inlet conduit 104, or a force originating elsewhere in container 103 and transmitted to inlet conduit 104). In examples, circuit elements 160 include a first circuit element electrically coupled to a second circuit element, and circuit 130 is configured to maintain the electrical coupling between the first circuit element and the second circuit element when circuit 130 flexes and/or bends with the flexible material, such that circuit 130 may generate heat prior to, during, and subsequent to a bending or flexure of the flexible material. In examples, circuit 130 is configured to flex and/or bend to maintain the electrical coupling between the first circuit element and the second circuit element when outer surface 158 of inlet conduit wall 154 deflects and/or a bends.

One or more of the circuit elements 160 may be configured to flex and/or bend when circuit 130 flexes and/or bends. In examples, circuit elements 160 include a conductive filament configured to flex and/or bend. In examples, some portion of the conductive filament defines the heating elements configured to generate the heat when circuit 130 receives the electrical power. The conductive filament may be configured to transfer heat to outer surface 158 of inlet conduit wall 154. In examples, the conductive filament contacts outer surface 158. In some examples, some portion of the conductive filament define the heating elements configured to generate the heat when circuit 130 receives the electrical power. The heating elements may be configured to transfer heat to outer surface 158 of inlet conduit wall 154 when circuit 130 receives the electrical power.

Circuit 130 may be configured to establish a thermal interface area with outer surface 158. The thermal interface area may be an area defined by some portion of outer surface 158. For example, the thermal interface area may be an area of outer surface 158 representing less than about 1%, less than about 10%, less than about 25%, less than about 50%, less than about 75%, or less than 100% of a total surface area defined by outer surface 158. Circuit 130 may be configured to transfer heat to the fluid within container volume 155 at least through the thermal interface area. In examples, circuit 130 is configured to generate a thermal flux from circuit 130 to container volume 155 through the thermal interface area when circuit 130 transfers the heat to the fluid within container volume 155.

In examples, circuit 130 is configured to substantially surround a perimeter defined by outer surface 158 of inlet conduit wall 154. Circuit 130 may be configured to contact outer surface 158 substantially around the perimeter. In some examples, the conductive filament of circuit 130 substantially surrounds the perimeter defined by outer surface 158. The conductive filament may substantially wrap around the perimeter to define a helix around inlet conduit 104. The conductive filament may define other geometries in other examples.

Control circuitry 132 may be configured to cause circuit 130 to generate the heat. In examples, control circuitry 132 is configured to provide the electrical power to circuit 130 to cause circuit 130 to generate the heat. Control circuitry 132 may provide the electrical power via, for example, conductor 162. In some examples, some portion or substantially all of control circuitry 132 is mechanically supported by some portion of container 103 and/or circuit 130. In some examples, some portion or substantially all of control circuitry 132 is mechanically supported by a housing 166 configured to remain physically displaced from container 103 and/or circuit 130. In examples, housing 166 mechanically supports electrical connector 165, and electrical connector 165 is configured to electrically couple circuit 130 and control circuitry 132 when first electrical connector 164 mechanically mates with electrical connector 165. In examples, control circuitry 132 is configured to cause circuit 130 to alter a heat generation rate in order to, for example, alter the heat flux delivered to the fluid within container 103 (e.g., within container volume 155).

Control circuitry 132 may receive a temperature signal indicative of a temperature of the fluid from temperature sensor 134 and cause circuit 130 to generate the heat and/or alter a heat generation rate based on the indicative signal. In the example of FIG. 2, temperature sensor 134 is configured to sense a temperature of the fluid within a portion of inlet conduit 104, such as container volume 155. Control circuitry 132 may be configured to cause circuit 130 to generate the heat and/or alter the heat generation rate based on the indicated temperature of the fluid within inlet conduit 104. In examples, temperature sensor 134 is configured to sense a temperature of a fluid such as a solvent (e.g., purified water) in inlet conduit 104 prior to the fluid encountering a solute held within solute container 150. In other examples, temperature sensor 134 is configured to sense a temperature of the fluid at another location, such as a another location within container system 202 or a location displaced from container system 202, such as a location within medical machine 112 (FIG. 1).

Control circuitry 132 may be configured to receive the temperature signal from temperature sensor 134 via, for example, a communication link 168. In examples, communication link 168 is a hard-line (e.g., wired) communication link configured to electrically couple with control circuitry 132. In examples, communication link 168 includes a connector 172 configured to mechanically mate with a connector 174 configured to couple temperature sensor 134 and control circuitry 132. Housing 166 may mechanically support connector 174. In other examples, communication link 168 may be a wireless communication link.

In examples, control circuitry 132 is configured to compare the indicated fluid temperature from temperature sensor 134 to a temperature setpoint. Control circuitry 132 may be configured to receive the temperature setpoint via, for example, a communication link 176. Communication link 176 may be a hard-line or wireless communication link. Control circuitry 132 may be configured to cause circuit 130 to generate the heat and/or alter the heat generation rate based on the comparison of the indicated temperature from sensor 134 and the temperature setpoint. For example, if the indicated temperature is less than the temperature setpoint, then control circuitry 132 may cause circuit 130 to generate the heat and/or alter the heat generation rate such that the indicated temperature increases to substantially match (e.g., match or get closer to, such as within 1%-10% of) the temperature setpoint. If the indicated temperature is greater than the temperature setpoint, then control circuitry 132 may cause circuit 130 to cease generating heat and/or alter the heat generation rate such that the indicated temperature decreases to substantially match the temperature setpoint. In examples, the temperature setpoint is defined by a range of values around a central setpoint value, and the indicated temperature substantially matches the temperature setpoint when the indicated temperature is within the range of values.

In some examples, container system 202 includes a thermostat 178 configured to provide the temperature setpoint to control circuitry 132. Thermostat 178 may be configured to establish the temperature setpoint based on a communication from a medical machine (e.g., medical machine 112 (FIG. 1)), a user of container system 202, or another communication. In examples, thermostat 178 is configured to receive the temperature setpoint from a user interface such as a switch, a button, another input mechanism, a speaker configured to receive voice commands, a touch screen, or another device configured to receive a user input.

FIG. 3 illustrates an example container system 302 configured to transfer heat to a fluid within reservoir 106 defined by container body 108. Container body 108 includes a body wall 180. Body wall 180 may be wall of a medical solution bag configured to hold a medical solution within reservoir 106. Body wall 180 is an example of wall 128 (FIG. 1).

Body wall 180 defines a container volume 182 within reservoir 106 of container body 108. Container volume 182 may be fluidly coupled to the lumen within inlet conduit 104 and the lumen within outlet conduit 110. Body wall 180 includes a flexible material configured to flex and/or bend. The flexible material may define body wall 180. Body wall 180 may be configured such that the flexible material deflects and/or bends in response to a force applied to body wall 180, or a force originating elsewhere in container 103 and transmitted to body wall 180 (e.g., due to movement of some portion of container system 302 from flow of a fluid, inadvertent contact by another object or a person, or some other reason).

Body wall 180 is configured to transfer heat to a fluid within container volume 182. In examples, body wall 180 defines an inner wall surface 184 defining a boundary of container volume 182 and an outer wall surface 186 opposite inner wall surface 184. Inner wall surface 184 may be configured to contact a fluid within container volume 182 to transfer heat to the fluid (e.g., by convection). Inner wall surface 184 is configured such that heat may transfer from outer wall surface 186, through body wall 180, and to inner wall surface 184 when body wall 180 transfers heat to the fluid within container volume 182. In examples, body wall 180 is configured to transfer heat through the flexible material comprising body wall 180 when body wall 180 transfers heat to the fluid within container volume 182. Outer wall surface 186 may be an exterior surface of container body 108.

Circuit 130 is configured to generate heat and transfer the heat to inner wall surface 184, such that inner wall surface 184 may transfer the heat to the fluid within container volume 182. Circuit 130 is configured to generate the heat using circuit elements 160. One or more of the circuit elements 160 may be configured to flex and/or bend when body wall 180 (e.g., the flexible material) flexes and/or bends. In examples, circuit elements 160 include a conductive filament configured to transfer heat to outer wall surface 186. The conductive filament may contact outer wall surface 186. In examples, circuit elements 160 include heating elements configured to transfer heat to outer wall surface 186 when circuit 130 receives the electrical power.

Circuit 130 may be configured to establish a thermal interface area with outer wall surface 186. The thermal interface area may be an area defined by some portion of outer wall surface 186. For example, the thermal interface area may be an area of outer wall surface 186 representing less than about 1%, less than about 10%, less than about 25%, less than about 50%, less than about 75%, or less than 100% of a total surface area defined by outer wall surface 186. Circuit 130 may be configured to transfer heat to the fluid within container volume 182 at least through the thermal interface area. In examples, circuit 130 is configured to generate a thermal flux from circuit 130 to container volume 182 through the thermal interface area when circuit 130 transfer the heat to the fluid within container volume 182.

As discussed, control circuitry 132 may be configured to receive a temperature signal indicative of a temperature of the fluid from temperature sensor 134 and cause circuit 130 to generate the heat and/or alter a heat generation rate based on the indicative signal. In the example of FIG. 3, temperature sensor 134 is configured to sense a temperature of the fluid within a portion of reservoir 106, such as container volume 182. Control circuitry 132 may be configured to cause circuit 130 to generate the heat and/or alter the heat generation rate based on the indicated temperature of the fluid within reservoir 106. In examples, temperature sensor 134 is configured to sense a temperature of a fluid such as a medical solution in reservoir 106 prior to container system 302 delivering the fluid to a medical machine (e.g., medical machine 112 (FIG. 1)) and/or a patient. In other examples, temperature sensor 134 may be configured to sense a temperature of the fluid at another location within container system 302 or a location displaced from container system 302, such as a location within medical machine 112.

FIG. 4 illustrates an example container system 402 configured to transfer heat to a fluid within outlet conduit 110 of container 103. Outlet conduit 110 of container system 302 includes an outlet conduit wall 188. Outlet conduit wall 188 is an example of wall 128 (FIG. 1). Outlet conduit wall 188 defines a container volume 190 within the lumen of outlet conduit 110. Container volume 190 may be fluidly coupled to reservoir 106. Outlet conduit wall 188 includes a flexible material configured to flex and/or bend. The flexible material may define outlet conduit wall 188. In examples, outlet conduit 110 is flexible tubing and outlet conduit wall 188 is a wall of the tubing. Outlet conduit wall 188 may be configured such that the flexible tubing of outlet conduit 110 deflects and/or bends in response to a force applied to outlet conduit 110 or a force originating elsewhere in container 103 and transmitted to outlet conduit 110.

Outlet conduit wall 188 is configured to transfer heat to a fluid within container volume 190. In examples, outlet conduit wall 188 defines an inner surface 192 defining the lumen of outlet conduit 110 and an outer surface 194 opposite inner surface 192. Inner surface 192 may be configured to contact a fluid flowing within container volume 190 to transfer heat to the fluid (e.g., by convection). Outlet conduit wall 188 is configured such that heat may transfer from outer surface 194, through outlet conduit wall 188, and to inner surface 192 when outlet conduit wall 188 transfers heat to the fluid within container volume 1190. In examples, outlet conduit wall 188 is configured to transfer heat through the flexible material comprising outlet conduit wall 188 when outlet conduit wall 188 transfers heat to the fluid within container volume 190. Outer surface 194 may be an exterior surface of outlet conduit 110.

Circuit 130 is configured to generate heat and transfer the heat to inner surface 192, such that inner surface 192 may transfer the heat to the fluid within container volume 190. Circuit 130 is configured to generate the heat using circuit elements 160. One or more of the circuit elements 160 may be configured to flex and/or bend when outlet conduit wall 188 (e.g., the flexible material) flexes and/or bends. In examples, circuit elements 160 include a conductive filament configured to transfer heat to outer surface 194. The conductive filament may contact outer surface 194. In examples, circuit elements 160 include heating elements configured to transfer heat to outer surface 194 when circuit 130 receives the electrical power.

Circuit 130 may be configured to establish a thermal interface area with outer surface 194. The thermal interface area may be an area defined by some portion of outer surface 194. For example, the thermal interface area may be an area of outer surface 194 representing less than about 1%, less than about 10%, less than about 25%, less than about 50%, less than about 75%, or less than 100% of a total surface area defined by outer surface 194. Circuit 130 may be configured to transfer heat to the fluid within container volume 190 at least through the thermal interface area. In examples, circuit 130 is configured to generate a thermal flux from circuit 130 to container volume 190 through the thermal interface area when circuit 130 transfer the heat to the fluid within container volume 190.

Control circuitry 132 may be configured to receive a temperature signal indicative of a temperature of the fluid from temperature sensor 134. In the example of FIG. 4, temperature sensor 134 is configured to sense a temperature of the fluid within outlet conduit 110, such as container volume 190. Control circuitry 132 may be configured to cause circuit 130 to generate the heat and/or alter the heat generation rate based on the indicated temperature of the fluid within outlet conduit 110. In examples, temperature sensor 134 is configured to sense a temperature of a fluid such as a medical solution in outlet conduit 110 prior to container system 402 delivering the fluid to a medical machine (e.g., medical machine 112 (FIG. 1)) and/or a patient. In other examples, temperature sensor 134 may be configured to sense a temperature of the fluid at another location within container system 402 or a location displaced from container system 402, such as a location within medical machine 112.

FIG. 5 illustrates an example container system 502 configured to define a covering 196 configured to transfer heat to a fluid within container 103. Covering 196 mechanically supports circuit 130. Covering 196 may be configured to substantially cover some portion of container 103, such as a portion of container body 108. In examples, covering 196 defines a cavity (e.g., a pocket or pouch) configured to receive a portion of container 103 when covering 196 transfers heat to the fluid within container 103. Covering 196 may be configured to substantially wrap around some portion of container 103 (e.g., a portion of container body 108, inlet conduit 104, and/or outlet conduit 110).

Covering 196 includes a cover wall 198 configured to transfer heat to a fluid within a container volume 204 defined by container 103. Cover wall 198 is an example of wall 128 (FIG. 1). In examples, container volume 204 is defined by one or more of container body 108, inlet conduit 104, and/or outlet conduit 110. Container volume 204 may be fluidly coupled to the lumen within inlet conduit 104, reservoir 106 defined by container body 108, and/or the lumen within outlet conduit 110.

Cover wall 198 may be configured to transfer heat to container 103 in order to heat the fluid within container volume 204. In examples, cover wall 198 defines an inner wall surface 206 configured to position adjacent container 103 (e.g., adjacent to container body 108, inlet conduit 104, and/or outlet conduit 110) and an outer wall surface 208 opposite inner wall surface 206. Inner wall surface 206 may be configured such that heat transfers from outer wall surface 208, through cover wall 198, and through inner wall surface 206 to container 103 when cover wall 198 transfers heat to the fluid within container volume 204. In examples, cover wall 198 is configured to transfer heat to a surface of container 103, such as outer wall surface 186 of container body 108, outer surface 194 of outlet conduit 110, and/or outer surface 158 of inlet conduit 104. In some examples, cover wall 198 is configured to contact some portion of outer wall surface 186, outer surface 194, and/or outer surface 158. Cover wall 198 may be configured to transfer heat to the surface of container 103 through any heat transfer mode, including conduction through a contact interface between inner wall surface 206 and a surface of container 103, convection via a heat transfer fluid between inner wall surface 206 and a surface of container 103, and/or radiation from inner wall surface 206 to a surface of container 103.

Cover wall 198 includes a flexible material configured to flex and/or bend. The flexible material may define cover wall 198. Cover wall 198 may be configured such that the flexible material deflects and/or bends in response to a force applied to cover wall 198, or a force originating somewhere on container 103 and transmitted to cover wall 198 by container system 102. In examples, cover wall 198 is configured to transfer heat through the flexible material comprising cover wall 198 when cover wall 198 transfers heat through container 103 to heat the fluid within container volume 204.

Circuit 130 is configured to generate heat and transfer the heat to inner wall surface 206, such that inner wall surface 206 may transfer the heat through container 103 to the fluid within container volume 204. Circuit 130 is configured to generate the heat using circuit elements 160. One or more of the circuit elements 160 may be configured to flex and/or bend when cover wall 198 (e.g., the flexible material) flexes and/or bends. In examples, circuit elements 160 include a conductive filament configured to transfer heat to outer wall surface 208. The conductive filament may contact outer wall surface 208. In examples, circuit elements 160 include heating elements configured to transfer heat to outer wall surface 208 when circuit 130 receives the electrical power.

As discussed, control circuitry 132 may be configured to receive a temperature signal indicative of a temperature of the fluid from temperature sensor 134 and cause circuit 130 to generate the heat and/or alter a heat generation rate based on the indicative signal. In the example of FIG. 4, temperature sensor 134 is configured to sense a temperature of the fluid within a portion of outlet conduit 110, however temperature sensor 134 may be configured to sense a temperature of a fluid at another location within container system 402 or a location displaced from container system 402, such as a location within medical machine 112. In examples, container 103 is configured to cause a fluid to flow from a first location of container 103 downstream to a second location of container 103, and container system 402 is configured to transfer heat to the fluid using covering 196 at the first location and sense a temperature of the fluid using sensor 134 at the second location. In examples, temperature sensor 134 is configured to sense a temperature of a fluid such as a medical solution within container system 502 prior to container system 502 delivering the fluid to a medical machine (e.g., medical machine 112 (FIG. 1)) and/or a patient.

Control circuitry 132 may be configured to cause circuit 130 of container system 102, 202, 302, 402, 502 to generate heat and/or alter a heat generation rate based on the temperature signal from temperature sensor 134 and one or more additional signals indicative of a fluid parameter. The one or more additional signals may include, for example, a second temperature signal from a second temperature sensor configured to sense a temperature indicative of a fluid in container system 102, 202, 302, 402, 502, or elsewhere, a flow rate signal indicative of a mass and/or volumetric flow of the fluid through container 103, medical machine 112, or some other fluid parameter. The one or more additional signals may include be indicative of a fluid parameter of a second fluid which mixes with the fluid flowing through container system 102, 202, 302, 402, 502, such as a second fluid flowing within machine inlet conduit 114, machine fluid line 116, conditioning system 120, and/or another portion of medical machine 112 or another medical machine. The one or more additional signals may include be indicative of a fluid parameter of a fluid mixture comprising the fluid from container system 102, 202, 302, 402, 502, such as fluid mixture flowing within generation flow path 122, mixing system 144, infusion line 118, and/or a fluid mixture flowing within another portion of medical machine 112 or another medical machine.

In some examples, control circuitry 132 is configured to utilize the temperature signal of temperature sensor 134 in order to determine a temperature of the fluid or a fluid mixture comprising the fluid at a location substantially downstream or upstream from temperature sensor 134. For example, control circuitry 132 may be configured to determine the temperature at the downstream or upstream location using the temperature signal from temperature sensor 134 as a value in one or more equations that generate a solution representative of the temperature at the downstream or upstream location. Control circuitry 132 may be configured to cause circuit 130 to generate heat and/or alter a heat generation rate based on the generated solution. For example, temperature sensor 134 may be configured to transmit a particular temperature signal indicative of a temperature of the fluid within container 103 to control circuitry 132, and control circuitry 132 may be configured to use the particular temperature signal to determine a temperature of a fluid within generation flow path 122, infusion line 118, or some other flow path defined by medical machine 112 (FIG. 1). Control circuitry 132 may be configured to cause circuit 130 to generate heat and/or alter a heat generation rate based on the determined temperature of a fluid within generation flow path 122, infusion line 118, or the other flow path.

FIG. 6 illustrates a container system 602 including circuit 130 mechanically supported by a flexible material 210 comprising a flexible wall 212. Container system 602 is an example of container system 102, 202, 302, 402, 502. Circuit 130 includes circuit elements 160 including conductive filaments 214 and 216. Conductive filaments 214, 216 are configured to receive electrical power via conductor 162 from control circuitry 132 and generate heat using the electrical power, such that control circuitry 132 causes circuit 130 to generate heat. Circuit 130 is configured to transfer the generated heat through flexible wall 212 to a fluid within a container volume 218. In examples, flexible wall 212 defines a boundary of container volume 218. Wall 212 is an example of wall 128, inlet conduit wall 154, body wall 180, outlet conduit wall 188, and/or cover wall 198. Container volume 218 is an example of container volume 155, container volume 182, container volume 190, and/or container volume 204.

Conductive filaments 214, 216 include a conductive material capable of conducting an electrical current driven by the electrical power received via conductor 162. The conductive material may be a metal (e.g., silver), a ceramic, or some other conductive material (e.g., graphene). In examples, conductive filaments 214, 216 are resistive heating elements configured to generate heat when conductive filaments 214, 216 conduct the electrical current. In some examples, conductive filaments 214, 216 are configured to deliver electrical power received via conductor to one or more heating elements within circuit 130. Conductive filament 214 may be electrically connected to conductive filament 216 and/or another component of circuit 130 (e.g., a heating element). Circuit 130 may be configured to maintain the electrical connectivity between conductive filament 214, conductive filament 214, and/or the other component of circuit 130 when circuit 130 flexes and/or bends with flexible material 210.

In examples, one or more of the circuit elements 160 (e.g., one or more of conductive filaments 214, 216) contact an outer surface 220 of flexible wall 212. Outer surface 220 is an example of outer surface 158 of inlet conduit 104, outer wall surface 186 of container body 108, outer surface 194 of outlet conduit 110, and/or outer wall surface 208 of covering 196. In examples, one or more of circuit elements 160 are substantially adhered to outer surface 220, such that movement of outer surface 220 (e.g., due to movement of flexible wall 212) causes a corresponding movement of the one or more of circuit elements 160. In some examples, one or more of circuit elements 160 substantially adhere to outer surface 220 due to a surface roughness of the one or more of circuit elements 160 and/or outer surface 220. For example, one or more of circuit elements 160 may be configured such that asperities defined by a surface of the one or more of circuit elements 160 mechanically engage asperities defined by outer surface 220 to cause one or more of circuit elements 160 to substantially adhere to outer surface 220. In some examples, one or more of circuit elements 160 form a bonded interface with flexible wall 212 to cause conductive filaments 214, 216 to substantially adhere to outer surface 220. In some examples, container system 602 includes an interlayer between one or more of circuit elements 160 and outer surface 220 with the one or more of circuit elements 160 substantially adhered to the interlayer. The interlayer may be substantially adhered to outer surface 220 to substantially adhere the one or more of circuit elements 160 (e.g., conductive filaments 214, 216) to outer surface 220.

Circuit 130 may include conductive filaments such as conductive filament 214, 216 arranged in any manner. In some examples, a conductive filaments 214, 216 are arranged to define a single layer on outer surface 220. In other examples, conductive filaments are arranged to define multiple layers on outer surface 220. For example, a first conductive filament (e.g., conductive filament 214) may comprise a first layer of conductive filaments and a second conductive filament (e.g., conductive filament 216) may define a second layer of conductive filaments. Circuit 130 may be configured such that the first layer is between the second layer and outer surface 220.

Circuit 130 may be fabricated in any manner sufficient to cause flexible material 210 to mechanically support circuit 130. In examples, circuit 130 is a 3-D printed circuit. Circuit 130 may be fabricated by using a 3-D printer to distribute a printing ink comprising a conductive material on outer surface 220 to form conductive filaments 214, 216. Circuit 130 may be fabricated by embedding and/or hot pressing one or more of circuit elements 160 into outer surface 220. In examples, circuit 130 may be fabricated by adhering one of more of circuit elements 160 to outer surface 220 using an adhesive. Circuit 130 may be fabricated in any manner sufficient to allow circuit 130 to flex and/or bend when flexible material 210 flexes and/or bends.

FIG. 7 illustrates a container system 702 including circuit 130 having a circuit substrate 222 supporting one or more of circuit elements 160, such as conductive filaments 214, 216. Circuit substrate 222 is mechanically supported by flexible material 210 comprising flexible wall 212. Container system 702 is an example of container system 102, 202, 302, 402, 502, 602. Circuit 130 may be configured to transfer heat generated by circuit elements 160 through circuit substrate 222, in order to transfer heat through flexible wall 212 to a fluid within a container volume 218.

Circuit substrate 222 may be configured to flex and/or bend when flexible material 210 of flexible wall 212 flexes and/or bends. In examples, circuit substrate 222 is configured to flex and/or bend when outer surface 220 of flexible wall 212 flexes and/or bends. In examples, Circuit substrate 222 contacts outer surface 220. Circuit substrate 222 may be substantially adhered to outer surface 220, such that movement of outer surface 220 causes a corresponding movement of circuit substrate 222. For example, circuit substrate 222 may substantially adhere to outer surface 220 due to a surface roughness of circuit substrate 222 and/or outer surface 220. Circuit substrate 222 may be configured such that asperities defined by a surface of circuit substrate 222 mechanically engage asperities defined by outer surface 220 to cause the adherence. In some examples, circuit substrate 222 forms a bonded interface with flexible wall 212 to cause the adherence. In some examples, container system 602 includes an interlayer between circuit substrate 222 and outer surface 220, with circuit substrate 222 and/or outer surface 220 substantially adhered to the interlayer. In some examples, the interlayer is an adhesive element configured to cause an adhesive of the adhesive layer to adhere to circuit substrate 222 and/or outer surface 220.

In examples, circuit substrate 222 comprises an insulative material configured to insulate one or more of circuit elements 160 (e.g., conductive filaments 214, 216) from at least outer surface 220. Circuit substrate 222 may be configured to mechanically support one or more of circuit elements 160. In examples, circuit substrate 222 defines one or more trace channels configured to mechanically support one or more of circuit elements 160, such as conductive filament 214, 216. The trace channels may be configured to substantially surround and/or contact some portion of conductive filament 214, 216 to mechanically support conductive filament 214, 216.

Circuit substrate 222 may be fabricated in any manner sufficient to cause circuit substrate 222 to support one or more of circuit elements 160. In examples, circuit substrate is a 3-D printed element fabricated by distributing (e.g., using a 3-D printer) a printing ink to fabricate one or more structures (e.g., a trace channel) of circuit substrate 222. In some examples, circuit substrate 222 is fabricated by milling one or more trace channels into a masking material comprising circuit substrate 222. Circuit 130 may be fabricated by positioning and/or fabricating a conductive filament (e.g., conductive filament 214, 216) in a trace channel. In some examples, circuit 130 is fabricated by co-depositing (e.g., using a 3-D printer) a first printing ink to fabricate circuit substrate 222 and a second printing ink to fabricate one or more of circuit elements 160. In examples, circuit 130 may be fabricated by embedding and/or hot pressing one or more of circuit elements 160 into a surface defined by circuit substrate 222. In examples, circuit 130 may be fabricated by adhering one of more of circuit elements 160 to circuit substrate 222 using an adhesive.

Figure 8:
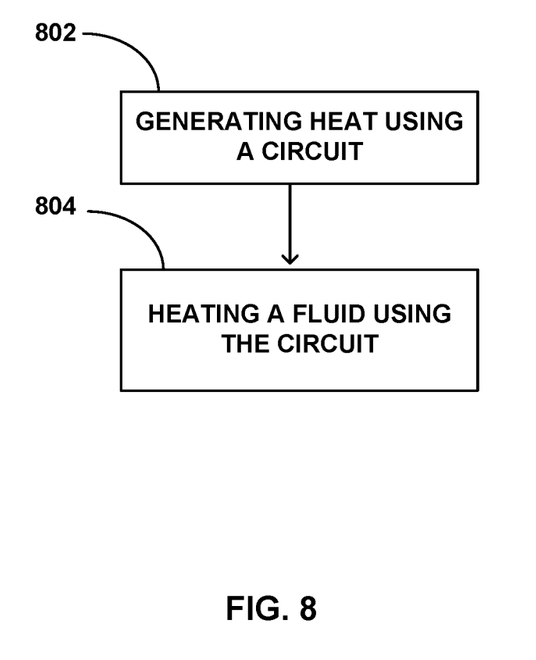
FIG. 8 is a flow diagram of an example technique of using a container system.

A technique for heating a fluid in a container 103 is illustrated in FIG. 8. Although the technique is described mainly with reference to container system 102, 202, 302, 402, 502, 602, 702, of FIGS. 1-7, the technique may be applied to other container systems in other examples.

The technique includes generating heat using a circuit 130 receiving electrical power (802). Circuit 130 is mechanically supported by a flexible material 210 Flexible material 210 may comprise wall 128, inlet conduit wall 154, body wall 180, outlet conduit wall 188, and/or cover wall 198. Circuit 130 is configured to configured to flex and/or bend when flexible material 210 flexes and/or bends. In examples, circuit 130 includes one or more circuit elements 160 electrically connected to a conductor 162 providing the electrical power to circuit 130, and the technique includes maintaining the electrical connection when circuit 130 flexes and/or bends.

The technique may include mechanically supporting circuit 130 using a flexible material comprising inlet conduit wall 154 of inlet conduit 104 of container 103. The technique may include mechanically supporting circuit 130 using a flexible material comprising body wall 180 of container body 108 of container 103. The technique may include mechanically supporting circuit 130 using a flexible material comprising outlet conduit wall 188 of outlet conduit 110 of container 103. In examples, the technique includes mechanically supporting circuit 130 using a flexible material comprising cover wall 198 of covering 196.

The technique may include transferring the heat generated by circuit 130 through wall 128, inlet conduit wall 154, body wall 180, outlet conduit wall 188, and/or cover wall 198 to a fluid within a container volume 155, 182, 190, 204, 218. Container volume 155, 182, 190, 204, 218 may be defined by container system 102, 202, 302, 402, 502, 602, 702. In examples, container 103 defines a boundary of container volume 155, 182, 190, 204, 218. Wall 128, inlet conduit wall 154, body wall 180, and/or outlet conduit wall 188 may define the boundary of container volume 155, 182, 190, 204, 218. In examples, the technique includes placing a cover wall 198 of a covering 196 configured to generate heat substantially adjacent to a portion of container 103 and transferring heat to container 103 to heat the fluid in container volume 155, 182, 190, 204, 218.

The technique may include generating the heat using one or more circuit elements 160 of circuit 130. In examples, circuit elements include one or more heating elements, such as resistive heating elements. The technique may include providing the electrical power to the one or more heating elements to cause the one or more heating elements to generate the heat. In examples, circuit elements 160 are configured to flex and/or bend when flexible material 210 flexes and/or bends. In examples, circuit elements comprises one or more conductive filaments 214, 216 configured to flex and/or bend when flexible material 210 flexes and/or bends.

The technique includes heating a fluid within container volume 155, 182, 190, 204 using the generated heat (804). The technique may include transferring the generated heat through wall 128, inlet conduit wall 154, body wall 180, outlet conduit wall 188, and/or cover wall 198 to heat a fluid within a container volume 155, 182, 190, 204, 218. In examples, the technique includes transferring the heat from circuit 130 through wall 128, inlet conduit wall 154, body wall 180, outlet conduit wall 188, and/or cover wall 198 using conductive heat transfer and transferring the heat to the fluid in container volume 155, 182, 190, 204, 218 using convective heat transfer.

The technique may include providing the electrical power to circuit 130 using control circuitry 132. In examples, the technique includes delivering a temperature signal indicative of a temperature of the fluid from temperature sensor 134 to control circuitry 132. The technique may include causing circuit 130 to generate the heat and/or alter a heat generation rate based on the temperature signal. In examples, the temperature signal is indicative of a temperature of a fluid with inlet conduit 104, reservoir 106 of container body 108, and/or outlet conduit 110. In examples, the temperature signal is indicative of a temperature of the fluid displaced from container system 402, such as a location within medical machine 112. In some examples, the technique includes delivering a temperature signal from temperature sensor 134 and an additional signal indicative of a parameter of a fluid from an additional sensor, and causing circuit 130 to generate the heat and/or alter a heat generation rate based on the temperature signal and the additional signal.

Control circuitry 132 may include any suitable arrangement of hardware, software, firmware, or any combination thereof, to perform the techniques attributed to control circuitry 132 herein. Examples of control circuitry 132 include any one or more microprocessors, digital signal processors (DSPs), application specific integrated circuits (ASICs), field programmable gate arrays (FPGAs), or any other equivalent integrated or discrete logic circuitry, as well as any combinations of such components. When control circuitry 132 includes software or firmware, control circuitry 132 further includes any necessary hardware for storing and executing the software or firmware, such as one or more processors or processing units. In general, a processing unit may include one or more microprocessors, DSPs, ASICs, FPGAs, or any other equivalent integrated or discrete logic circuitry, as well as any combinations of such components.

A temperature setpoint for container system 102, 202, 302, 402, 502, 602, 702 may be stored in a memory of control circuitry 132 or in another device communicatively coupled to control circuitry 132. The memory may include any volatile or non-volatile media, such as a random access memory (RAM), read only memory (ROM), non-volatile RAM (NVRAM), electrically erasable programmable ROM (EEPROM), flash memory, and the like. In addition, in some examples, the memory or another memory may also store executable instructions for causing control circuitry 132 described herein to perform the actions attributed to it.

Communication links 168, 176 may be hard-line and/or wireless communications links. Communication links 168, 176 may comprise some portion of control circuitry 132, thermostat 178, temperature sensor 134, and/or one another portion of another portion of container system 102, 202, 302, 402, 502, 602, 702. Communication links 168, 176 may comprise a wireless Internet connection, a direct wireless connection such as wireless LAN, Bluetooth, and/or an infrared connection. Communication links 168, 176 may utilize any wireless or remote communication protocol.

Temperature sensor 134 and/or other sensors described herein may be configured to generate a signal indicative of a fluid parameter at any location within medical system 100. Temperature sensor 134 and/or another sensor may be configured to generate the signal as a result of an interaction with a fluid and/or fluid mixture provided to and/or delivered by within container system 102, 202, 302, 402, 502, 602, 702. Temperature sensor 134 and/or another sensor may include a transducer configured to transduce the interaction into the signal indicative of a parameter of the fluid. The indicative signal may be an analog electrical signal or a digital signal. In some examples, temperature sensor 134 and/or another sensor may include processing circuitry configured to interpret a response of the transducer and generate the indicative signal, and/or control circuitry 132 may include processing circuitry configured to interpret a response of the transducer and generate the indicative signal. Temperature sensor 134 and/or another sensor may be configured to communicate the indicative signal indicative to other devices in data communication the temperature sensor 134 and/or another sensor.

The techniques described in this disclosure, including those attributed to control circuitry 132 and other control circuitry, processing circuitry, sensors, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in any suitable device. Processing circuitry, control circuitry, and sensing circuitry, as well as other processors, controllers, and sensors described herein, may be implemented at least in part as, or include, one or more executable applications, application modules, libraries, classes, methods, objects, routines, subroutines, firmware, and/or embedded code, for example. In addition, analog circuits, components, and circuit elements may be employed to construct one, some or all of the control circuitry and sensors, instead of or in addition to the partially or wholly digital hardware and/or software described herein. Accordingly, analog or digital hardware may be employed, or a combination of the two.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. The computer-readable medium may be an article of manufacture including a non-transitory computer-readable storage medium encoded with instructions. Instructions embedded or encoded in an article of manufacture including a non-transitory computer-readable storage medium encoded, may cause one or more programmable processors, or other processors, to implement one or more of the techniques described herein, such as when instructions included or encoded in the non-transitory computer-readable storage medium are executed by the one or more processors. Example non-transitory computer-readable storage media may include RAM, ROM, programmable ROM (PROM), erasable programmable ROM (EPROM), electronically erasable programmable ROM (EEPROM), flash memory, a hard disk, a compact disc ROM (CD-ROM), a floppy disk, a cassette, magnetic media, optical media, or any other computer readable storage devices or tangible computer readable media.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

The functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements.

The present disclosure includes the following examples.

Example 1: A container system for delivering a medical solution comprising a fluid for use in a patient, the container system comprising: a wall configured to transfer heat to a container volume configured to hold the fluid, wherein the wall comprises a flexible material; and a circuit mechanically supported by the flexible material, wherein the circuit is configured to flex with the flexible material, and wherein the circuit is configured to receive electrical power and generate heat using the electrical power to heat the fluid held within the container volume.

Example 2: The container system of example 1, wherein the wall defines the container volume.

Example 3: The container system of example 1 or example 2, wherein the circuit includes one or more circuit elements configured to generate the heat, wherein the one or more circuit elements are substantially adhered to the flexible material, and wherein the one or more circuit elements are configured to flex with the flexible material.

Example 4: The container system of any of examples 1-3, wherein the container system includes control circuitry configured to cause the circuit to generate the heat, wherein the control circuitry is configured to: receive a temperature signal indicative of a temperature of the fluid from a temperature sensor, and cause the circuit to generate the heat based on the temperature signal.

Example 5: The container system of example 4, further comprising the temperature sensor, wherein the temperature sensor is configured to sense a temperature of the fluid held within the container volume.

Example 6: The container system of example 4 or example 5, further comprising a thermostat configured to communicate a temperature setpoint to the control circuitry, wherein the control circuitry is configured to: compare the temperature setpoint and the temperature indicated by the temperature signal; and cause the circuit to generate the heat based on the comparison.

Example 7: The container system of any of examples 1-6, further comprising a container body defining a reservoir configured to hold a solute, wherein: the container system comprises an inlet conduit defining a flow path for the fluid into the reservoir, the container system is configured to cause the fluid to mix with the solute and form a solution in the reservoir, and the container system comprises an outlet conduit defining a flow path for the solution out of the reservoir.

Example 8: The container system of any of examples 1-7, further comprising: a container body defining a reservoir configured to contain the fluid; and a conduit defining a flow path in fluid communication with the reservoir, wherein a wall of the conduit defines the container volume, and wherein the flexible material comprises the wall of the conduit.

Example 9: The container system of any of examples 1-8, further comprising: a container body, wherein a wall of the container body defines the container volume, and wherein the flexible material comprises the wall of the container body; and one or more conduits defining a flow path in fluid communication with a reservoir defined by the container body.

Example 10: The container system of examples 9, wherein the one or more conduits include an inlet conduit and an outlet conduit, wherein the inlet conduit includes a first fluid connector configured to mechanically mate with a first machine connector of a machine to fluidly couple the inlet conduit and the machine, and wherein the outlet conduit includes a second fluid connector configured to mechanically mate with a second machine connector of the machine to fluidly couple the outlet conduit and the machine.

Example 11: The container system of any of examples 1-10, wherein the wall defines a covering configured to cover a portion of a container body defining the container volume, and wherein the circuit is configured to heat the fluid when the covering covers the portion of the container body.

Example 12: The container system of any of examples 1-11, wherein the circuit comprises one or more circuit elements and a circuit substrate mechanically supporting the one or more circuit element elements, wherein the wall mechanically supports the circuit substrate.

Example 13: The container system of any of examples 1-12, wherein an inner surface of the wall defines the container volume, wherein the circuit includes a one or more circuit elements configured to generate the heat, and wherein the one or more circuit elements contact with an outer surface of the wall.

Example 14: The container system of any of examples 1-13, wherein the circuit includes a first connector configured to mechanically mate with a second connector configured to provide the electrical power, wherein the first connector is configured to transfer the electrical power from the second connector to the circuit when the first connector mechanically mates with the second connector.

Example 15: A container system for heating and delivering a medical solution comprising a fluid for use in a patient, the container system comprising: a wall configured to transfer heat to a container volume configured to hold the fluid, wherein the wall comprises a flexible material; a circuit mechanically supported by the flexible material, wherein the circuit is configured to flex with the flexible material, and wherein the circuit is configured to receive electrical power and generate heat using the electrical power to heat the fluid held within the container volume; a temperature sensor configured to sense a temperature of the fluid held in the container volume; and control circuitry configured to cause the circuit to generate the heat, wherein the control circuitry is configured to: receive a temperature signal indicative of a temperature of the fluid sensed from the temperature sensor, and cause the circuit to generate the heat based on the temperature signal.

Example 16: The container of example 15, further comprising a thermostat configured to communicate a temperature setpoint to the control circuitry, wherein the control circuitry is configured to: compare the temperature setpoint and the temperature indicated by the temperature signal; and cause the circuit to generate the heat based on the comparison.

Example 17: The container system of example 15 or example 16, wherein the circuit comprises one or more circuit elements, wherein each circuit element of the one or more circuit elements are electrically connected to at least one other circuit element of the one or more circuit elements, and wherein the circuit is configured to sustain the electrical connection when the circuit flexes with the flexible material.

Example 18: The container system of any of examples 15-17, wherein the circuit includes a first connector configured to mechanically mate with a second connector configured to provide the electrical power, wherein the first connector is configured to transfer the electrical power from the second connector to the circuit when the first connector mechanically mates with the second connector.

Example 19: A method, comprising: generating heat using a circuit receiving electrical power and mechanically supported by a wall comprising a flexible material and defining a container volume holding a fluid; and heating the fluid in the container volume using the heat from the circuit.

Example 20: The method of example 19, further comprising: receiving, by the circuit, a temperature signal indicative of a temperature of the fluid from a temperature sensor; and generating the heat based on the temperature signal Various examples of the disclosure have been described. Any combination of the described systems, operations, or functions is contemplated. These and other examples are within the scope of the following claims.

What is claimed is:

1. A container system for delivering a medical solution comprising a fluid for use in a patient, the container system comprising:

a container body defining a fluid reservoir configured to hold the fluid, wherein the container body is configured to receive an inflow of the fluid into the fluid reservoir from an inlet conduit, and wherein the container body is configured to provide an outflow of the fluid from the fluid reservoir to an outlet conduit;

a cover wall defining a cavity configured to receive at least a portion of the container body, the cover wall configured to transfer heat to a volume of the container system configured to contain the fluid, wherein the cover wall comprises a flexible material, and wherein the cover wall is configured to transfer the heat from an inner wall surface of the cover wall to a surface of the portion of the container body when the cavity receives the portion of the container body;

a circuit mechanically supported by the flexible material, the circuit configured to heat the fluid when the cavity receives the portion of the container body, wherein the circuit is configured to flex with the flexible material, and wherein the circuit is configured to receive electrical power and generate the heat using the electrical power to cause the cover wall to transfer the heat to the fluid contained within the volume of the container system;

a temperature sensor configured to sense a temperature of the fluid, wherein the temperature sensor is configured to be positioned at a location displaced from the container body; and control circuitry configured to cause the circuit to generate the heat, wherein the control circuitry is configured to:
receive a temperature signal indicative of the temperature of the fluid from the temperature sensor, and
cause the circuit to generate the heat based on the temperature signal.

2. The container system of claim 1, wherein the circuit includes one or more circuit elements configured to generate the heat, wherein the one or circuit elements are substantially adhered to the flexible material, and wherein the one or more circuit elements are configured to flex with the flexible material.

3. The container system of claim 1, wherein the temperature sensor is configured to sense a temperature of the fluid held within the volume of the container system.

4. The container system of claim 1, further comprising a thermostat configured to communicate a temperature setpoint to the control circuitry, wherein the control circuitry is configured to:
compare the temperature setpoint and the temperature indicated by the temperature signal; and
cause the circuit to generate the heat based on the comparison of the temperature setpoint and the temperature indicated by the temperature signal.

5. The container system of claim 1, further comprising:
a solute within the fluid reservoir,
wherein the container system is configured to cause the inflow of the fluid to mix with the solute and form the medical solution in the fluid reservoir, and
wherein the container system is configured to provide an outflow of the medical solution to the outlet conduit.

6. The container system of claim 1, further comprising a conduit, wherein the conduit is one of the inlet conduit or the outlet conduit.

7. The container system of claim 1, wherein the volume of the container system is a portion of the fluid reservoir.

8. The container system of claim 7, further comprising:
the inlet conduit; and
the outlet conduit,
wherein the inlet conduit includes a first fluid connector configured to mechanically mate with a first machine connector of a machine to fluidly couple the inlet conduit and the machine, and
wherein the outlet conduit includes a second fluid connector configured to mechanically mate with a second machine connector of the machine to fluidly couple the outlet conduit and the machine.

9. The container system of claim 1, wherein the circuit includes a first connector configured to mechanically mate with a second connector configured to provide the electrical power, wherein the first connector is configured to transfer the electrical power from the second connector to the circuit when the first connector mechanically mates with the second connector.

10. A container system for heating and delivering a medical solution comprising a fluid for use in a patient, the container system comprising:
a container body including an inlet conduit and an outlet conduit, the container body defining a fluid reservoir configured to hold the fluid, wherein the container body is configured to receive an inflow of the fluid to the fluid reservoir from the inlet conduit, and wherein the container body is configured to provide an outflow of the fluid from the fluid reservoir to the outlet conduit;
a solute within the fluid reservoir, wherein the container system is configured to cause the inflow of the fluid to mix with the solute and form the medical solution in the fluid reservoir, and wherein the container system is configured to provide an outflow of the medical solution from the fluid reservoir to the outlet conduit;
a cover wall defining a cavity configured to receive at least a portion of the container body, the cover wall configured to transfer heat to a volume of the container system, wherein the cover wall comprises a flexible material, and wherein the cover wall is configured to transfer the heat from an inner wall surface of the cover wall to a surface of the portion of the container body when the cavity receives the portion of the container body;
a circuit mechanically supported by the flexible material, the circuit configured to heat the fluid when the cavity receives the portion of the container body, wherein the circuit is configured to flex with the flexible material, and wherein the circuit is configured to receive electrical power and generate the heat using the electrical power to cause the cover wall to transfer the heat to the fluid contained within the volume of the container system;
a temperature sensor configured to sense a temperature of the fluid, wherein the temperature sensor is configured to be positioned at a location displaced from the container body; and
control circuitry configured to cause the circuit to generate the heat, wherein the control circuitry is configured to:
receive a temperature signal indicative of a temperature of the fluid from the temperature sensor, and
cause the circuit to generate the heat based on the temperature signal.

11. The container of claim 10, further comprising a thermostat configured to communicate a temperature setpoint to the control circuitry, wherein the control circuitry is configured to:
compare the temperature setpoint and the temperature indicated by the temperature signal; and cause the circuit to generate the heat based on the comparison.

12. The container system of claim 10, wherein the circuit comprises one or more circuit elements, wherein each circuit element of the one or more circuit elements are electrically connected to at least one other circuit element of the one or more circuit elements, and wherein the circuit is configured to sustain the electrical connection between the circuit elements when the circuit flexes with the flexible material.

13. The container of claim 10, wherein the circuit includes a first connector configured to mechanically mate with a second connector configured to provide the electrical power, wherein the first connector is configured to transfer the electrical power from the second connector to the circuit when the first connector mechanically mates with the second connector.

14. A method, comprising:
receiving an inflow of a fluid from an inlet conduit into a fluid reservoir defined by a container body, wherein the container body is configured to provide an outflow of the fluid from the fluid reservoir to an outlet conduit;
generating heat using a circuit receiving electrical power and mechanically supported by a cover wall comprising a flexible material, wherein the cover wall is configured to transfer heat to a volume of the container system configured to contain the fluid;
heating, using the circuit, a portion of the fluid in the volume of the container system when at least a portion of the container body is received in a cavity defined by the cover wall, wherein heating the portion of the fluid comprises causing the cover wall to transfer the heat from an inner wall surface of the cover wall to a surface of the portion of the container body;
sensing a temperature of the fluid using a temperature sensor configured to be positioned at a location displaced from the container body;
receiving, using control circuitry, a temperature signal indicative of the temperature of the fluid from the temperature sensor; and
causing, using the control circuitry, the circuit to generate the heat based on the temperature signal.

15. The container system of claim 1, further comprising a conduit, wherein the conduit is one of the inlet conduit or the outlet conduit, and wherein the temperature sensor is configured to sense the temperature of the fluid within the one of the inlet conduit or the outlet conduit.

16. The container system of claim 1, wherein the temperature sensor is configured to sense the temperature of the inflow of the fluid into the fluid reservoir.

17. The method of claim 14, further comprising:
causing, using the container system, the inflow of the fluid to mix with a solute within the fluid reservoir to form a medical solution comprising the fluid in the fluid reservoir, and
providing an outflow of the medical solution from the fluid reservoir to the outlet conduit.

* * * * *